United States Patent

Gebhardt et al.

[11] Patent Number: 5,939,882
[45] Date of Patent: Aug. 17, 1999

[54] GRADIENT COIL ARRANGEMENT FOR A NUCLEAR MAGNETIC RESONANCE TOMOGRAPHY APPARATUS

[75] Inventors: Matthias Gebhardt; Franz Boemmel, both of Erlangen, Germany

[73] Assignee: Siemens Aktiengesellschaft, Munich, Germany

[21] Appl. No.: 08/995,322

[22] Filed: Dec. 22, 1997

[30] Foreign Application Priority Data

Dec. 20, 1996 [DE] Germany .......................... 196 53 449

[51] Int. Cl.$^6$ ........................................... G01V 3/00
[52] U.S. Cl. ............................................ 324/318
[58] Field of Search ................................ 324/318, 322, 324/300, 312, 307, 309, 314

[56] References Cited

U.S. PATENT DOCUMENTS

| 5,032,793 | 7/1991 | Yamamoto et al. | 324/309 |
| 5,177,441 | 1/1993 | Morich et al. | 324/318 |
| 5,198,769 | 3/1993 | Frese et al. | 324/318 |
| 5,309,107 | 5/1994 | Pausch | 324/309 |
| 5,497,089 | 3/1996 | Lampman et al. | 324/318 |
| 5,512,828 | 4/1996 | Pausch et al. | 324/309 |
| 5,574,373 | 11/1996 | Pausch et al. | 324/318 |

FOREIGN PATENT DOCUMENTS 0 313 213  4/1989  European Pat. Off. .

OTHER PUBLICATIONS

"Insertable Biplanar Gradient Coils for Magnetic Resonance Imaging," Martens et al., Rev. Sci. Instrum., vol. 62, No. 11, Nov. 1991, pp. 2639–2645.

Primary Examiner—Louis Arana
Attorney, Agent, or Firm—Hill & Simpson

[57] ABSTRACT

In a nuclear magnetic resonance tomography apparatus with ring coils for producing the basic magnetic field, effective portions of gradient coils are arranged on two radially spaced surfaces that lie symmetrical to the longitudinal axis of an examination chamber. The surfaces have in radial section, a curvature such that the distance between the two surfaces is greater in the center than at the edges.

7 Claims, 8 Drawing Sheets

GRADIENT COIL ARRANGEMENT FOR A NUCLEAR MAGNETIC RESONANCE TOMOGRAPHY APPARATUS

BACKGROUND OF THE INVENTION

1. Field of the Invention

The present invention relates to a gradient coil arrangement for a nuclear magnetic resonance tomography apparatus, in which a basic magnetic field is produced by ring coils that enclose an examination chamber and whose coil axes fie along a longitudinal axis of the examination chamber, wherein all the effective segments of the gradient coils are arranged respectively on two radially spaced surfaces that lie symmetrical to the longitudinal axis of the examination chamber, so that the gradient coil arrangement remains open laterally.

2. Description of the Prior Art

A gradient coil arrangement of this type is known, for example, from the article by M. A. Martens et al., "Insertable biplanar gradient coils for magnetic resonance imaging," Review of Scientific Instrumentation 62(11), November 1991, pages 2639 to 2645. This article relates to coils known as "local" gradient coil arrangements, which typically are not installed fixedly in the MR apparatus, but rather are inserted only given the examination of particular body parts (e.g. the head). Since such local gradient coil arrangements can enclose a smaller examination volume than fixedly installed gradient coil arrangements, the magnetic energy stored therein becomes correspondingly smaller. It is thereby possible to achieve correspondingly shorter rise and fall times of the gradient pulses, with the same demands on the gradient coils and the gradient amplifier being operated the same as for a fixed coil. Local gradient coils are thus suited in particular for pulse sequences in which gradients have to be switched very rapidly, e.g. for the EPI (echoplanar imaging) method.

In the gradient coil arrangement described in the above article, this arrangement is deployed on two parallel plates containing all the gradient coils required for the gradient field production in three directions. The plate-shaped structures can be brought into close proximity to the subject under examination, so that the magnetic energy stored essentially between these plates remains lower than in conventional whole-body arrangements.

Figure 1:
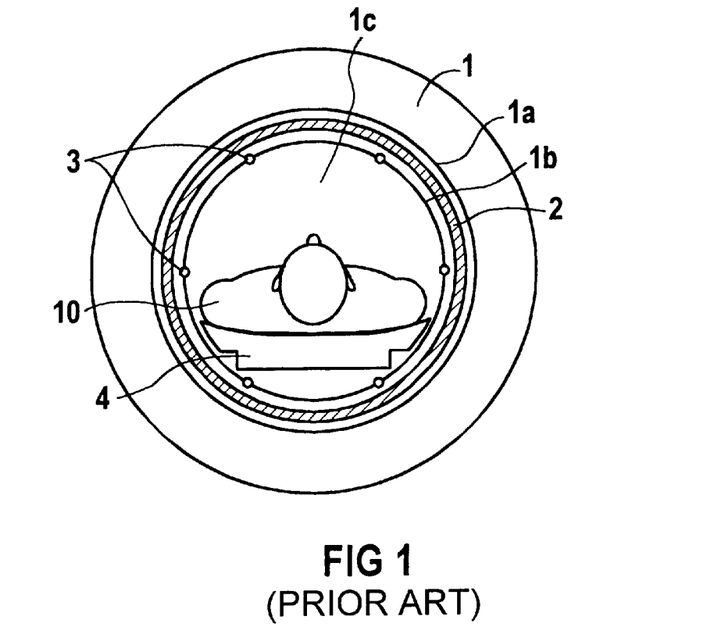
FIG. 1, as noted above, is a schematic sectional view of a known magnetic resonance imaging apparatus, showing a conventional gradient coil arrangement therein.

Conventional, fixedly installed gradient coil arrangements occupy a considerable portion of the interior space of a magnet arrangement (called the "warm bore" in superconducting magnets). This is explained in more detail with the help of FIG. 1. FIG. 1 shows a highly schematic representation of the components of a nuclear magnetic resonance tomograph. The basic magnetic field is produced with a magnet 1 in a ring coil arrangement that is constructed in superconducting fashion. In superconducting basic field magnets, the coils (not shown in FIG. 1) are arranged in a cryostatic temperature regulator. The basic field magnet has a hollow cylindrical interior space. A gradient coil arrangement 2 with a hollow cylindrical shape is arranged in this interior space. A radio-frequency antenna 3 is provided inside the gradient coil arrangement 2. The interior space remaining after the installation of the gradient coil arrangement 2 and the RF antenna 3, and after the assembly of sheathings (not shown), is available as useful space. A patient 10 can be placed in this useful space on a patient table 4. For the useful space, certain minimum dimensions are required, particularly with respect to the width, in order to enable the examination of patients in general with a certain degree of comfort in their positioning, and to enable overweight patients to be examined at all. The required inner diameter of the basic field magnet is thus given by the desired dimensions of the useful space, as well as by the radial extension of the RF antenna 3 and the gradient coil arrangement 2. The inner diameter of the basic field magnet 1, however, determines its cost. It is necessary to construct not only the ring coils, and also the cryostatic temperature regulator in superconducting systems, with a larger diameter. It is also necessary to apply more magnetic energy at a given magnetic field strength, due to the larger interior volume. Given constant preconditions relating to the required homogeneity in the examination chamber, with a larger inner diameter of the basic field magnet the length thereof must also be increased. This is not only highly undesirable from the point of view of cost, but also causes increased claustrophobia problems in the patients, and worsens accessibility to the patient.

Of the systems installed in the examination chamber of the basic field magnet 1, the gradient coil arrangement has the largest space requirement.

Figure 2:
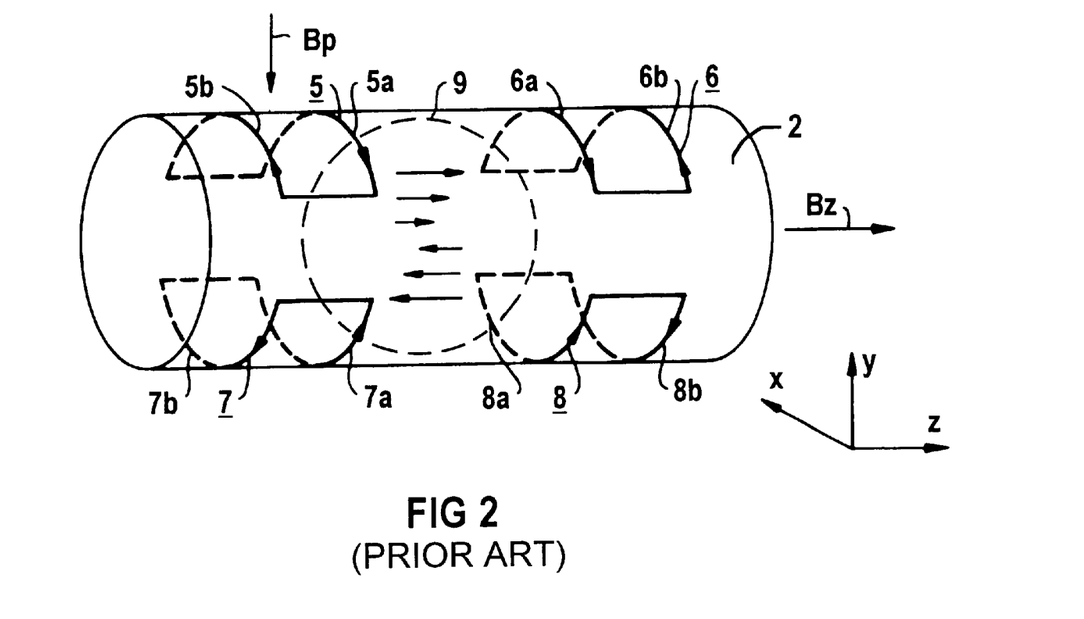
FIG. 2, as noted above, is a schematic perspective view of coils of a conventional gradient coil arrangement for producing a magnetic field gradient in the y-direction.

For the explanation of the basic problem to which the present invention is directed, in FIG. 2 a conventional gradient coil system for producing a magnetic field gradient in the y-direction is schematically shown. In nuclear magnetic tomography apparatuses, magnetic field gradients in three directions (x, y and z) perpendicular to one another, corresponding to the coordinate system shown in FIG. 2, are required. The direction of the basic magnetic field $B_z$, i.e. the longitudinal axis of the hollow cylindrical examination chamber, is defined as the z-direction. FIG. 2 shows only the gradient coil system of conventional construction used to produce a magnetic field gradient in the y-direction. This gradient coil system consists of four individual saddle coils 5 to 8. The inner curves 5a to 8a of the saddle coils essentially contribute to the production of the magnetic field gradient in the y-direction, called the y-gradient for short in the following; the outer curves 5b to 8b lie at a greater distance from the spherical examination region 9, for which both the homogeneity requirements concerning the basic magnetic field and linearity requirements concerning the gradient fields must be maintained. The effect of the inner curves 5a to 8a on the magnetic field in the spherical region of examination 9 is indicated in FIG. 2 with arrows. In the upper part of the region of examination 9, an amplification of the basic magnetic field $B_z$ is achieved, and in the lower region an attenuation of this field is achieved, so that a magnetic field gradient in the y-direction arises. For the production of a magnetic field gradient in the x-direction, the same coil arrangement is again present, but rotated 90° about the cylinder axis, but is not shown in FIG. 2 for clarity. Finally, for the production of a magnetic field gradient in the z-direction, ring coils (also omitted in FIG. 2 for clarity) are arranged on the cylindrical support (carrier).

It should be noted that more modern gradient coil arrangements are no longer constructed from simple segment curves. Rather, more complex conductor structures, resembling a fingerprint, arise as a result of optimization methods, as described for example in U.S. Pat. No. 5,309,107. This has no effect, however, on the basic problem described herein.

Even when the individual gradient coils are of relatively flat construction, a non-negligible thickness of the overall gradient coil arrangement results from the necessity of stacking three coil structures over one another. This is particularly so when gradient shielding coils are present that are intended to prevent the occurrence of eddy currents in the metallic outer wall of the examination chamber 1c by outwardly compensating gradient fields. Gradient coils of this sort, called "actively shielded," are shown for example in German OS 44 22 782. Moreover, the distance between the useful portion of the gradient coil and the gradient shielding coil is reduced outwardly in order to reduce the parasitic flux density. In an embodiment described in this publication, the available examination chamber is thereby further expanded outwardly by expansion (widening) of the gradient useful coils.

From German OS 195 04 171, a local gradient coil arrangement for a nuclear magnetic resonance tomography apparatus is described that has a substantially hollow cylindrical geometry, as do conventional gradient coils. In order to enable simpler application of the local gradient coil arrangement to an examination subject, it can be separated at least on one side along a separation line that runs in the axial direction. The coil design itself corresponds in principle to the conventional gradient coil, but all the gradient coil conductors that cross the separating line are interrupted at the separating line. On each side of the separating line, the currents are conducted via connection leads that run parallel to the line of separation.

Finally, from European Application 0 313 213 a gradient coil arrangement is known in which one of the gradient coils, namely the y-gradient coil, lies closer to the examination subject than do the other gradient coils. A stronger gradient field thus can be produced in the y-direction, with otherwise identical preconditions.

SUMMARY OF THE INVENTION

An object of the present invention is to provide a gradient coil arrangement of the general type initially described wherein the inner diameter of the basic field magnet, and thus the basic field magnet as a whole, can be made smaller, without significantly reducing the same capacity of the useful space available for patients. In addition, the sensitivity of the gradient coil should be increased. "Sensitivity" means the ratio of the gradient field produced to the current to be applied, given the same number of windings. Stated from another viewpoint, a lower inductance and power consumption are to be achieved, with the same sensitivity.

This object is achieved according to the invention in a gradient coil arrangement wherein the surfaces on which the useful portions of the gradient coils are arranged have a curvature in radial section (i.e., in a radial plane) such that the distance between the two surfaces is greater in the center than at the edges. Due to the distance between the two surfaces, additional space arises laterally in the center of the examination chamber, so that the inner diameter of the magnet can be reduced correspondingly. In addition, by means of the curvature of the above-described surfaces, the sensitivity (as defined above) is improved.

The curvature of the surfaces is smaller than that of an outer wall of the examination chamber. A better adaptation to the body shape of the patient is thereby achieved, which in turn has a positive effect on the sensitivity.

In addition, in axial section (i.e., in an axial plane) the surfaces are curved such that in the center of the examination chamber they have a smaller distance to one another than at the edge. By means of the outward expansion of the gradient coil arrangement, the sensitivity is likewise improved. The return conductors, which have a smaller destructive effect on the useful field when they are at a larger distance from the examination subject, are always routed in the outer regions of the gradient coil arrangement, seen in the longitudinal direction. In addition, an outwardly widening arrangement of the gradient coils is more comfortable for the patient, with respect to problems of claustrophobia.

Eddy currents caused by switched gradients can be significantly reduced if gradient shielding coils are provided that are arranged in the proximity of an outer wall that surrounds the examination chamber. Due to the vicinity to the metallic outer wall, the effect of the shielding coil is improved, and in addition the destructive effect of the gradient shielding coil on the gradient field is reduced by the increased distance between the effective portion of the gradient coil and the gradient shielding coil.

Cooling ducts can be arranged in the intermediate space between the effective portions of the gradient coils and the gradient shielding coils. Since sufficient space is now made available there, the provision of ducts is possible without an additional space requirement.

The useful portions of the gradient coils and gradient shielding coils required for each spatial direction can be interleaved with one another. This permits a simple manufacture with a small space outlay.

For particular applications, it is advantageous if the useful-field-producing conductors of the gradient useful coils are routed so that the examination region of the gradient coil arrangement lies asymmetrically in the direction of the longitudinal axis. The examination subject thus need not be introduced into the center of the gradient coil system, but rather only to the edge of the system. Claustrophobia problems, e.g. during head examinations, can thereby be reduced. In addition, in specific systems (as an example, apparatuses for head examinations) the diameter of the examination region is kept smaller than would be required for an exposure of the entire body.

DESCRIPTION OF THE PREFERRED EMBODIMENTS

Figure 3:
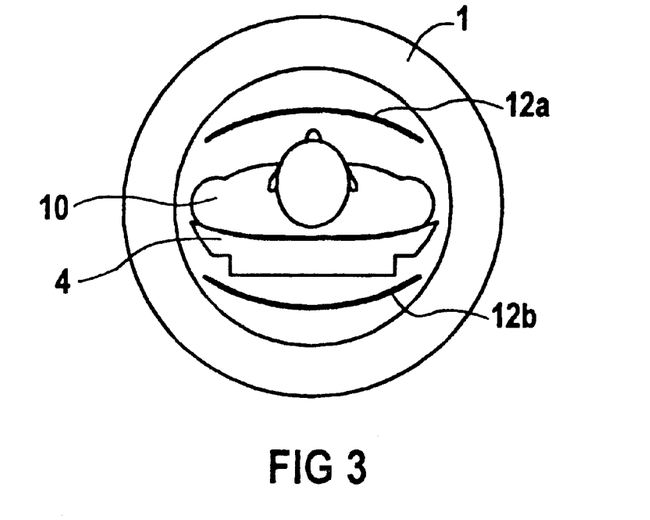
FIG. 3 shows a schematic sectional view of a first exemplary embodiment of a magnetic resonance apparatus having an inventive gradient coil apparatus.

In the schematic representation of an exemplary embodiment of the invention according to FIG. 3, the two curved surfaces 12a and 12b can be seen on which the gradient coil system is arranged. The curved surfaces 12a and 12b have lateral openings, so that for the patient 10, and, as needed, for the patient bed 4, there is more space available laterally than in conventional gradient coil systems in the form of a closed circular cylinder. The surrounding magnet thus can be of smaller construction, so that corresponding advantages arise with respect to the cost, the structural volume, the weight, etc. Measurements have shown that the sensitivity of the gradient coil arranged on a curved surface is better than that of a gradient coil correspondingly arranged on two parallel plates in the prior art. "Sensitivity" means the field strength achieved with otherwise equal preconditions and at a particular current. From another point of view, at the same sensitivity a lower inductance and power consumption are achieved. This is connected among other things with the fact that the volume enclosed by the curved surfaces is smaller than that between two parallel plates.

Figure 4:
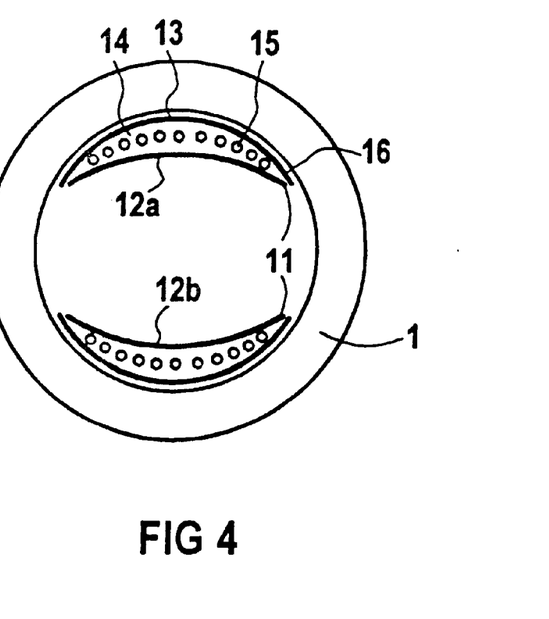
FIG. 4 shows a schematic sectional drawing of a further exemplary embodiment of a first exemplary embodiment of a magnetic resonance apparatus having an inventive gradient coil apparatus with gradient shielding coils.

For the avoidance, in particular, of eddy currents in the metallic inner walls of the magnet 1, the gradient coil arrangement can be constructed with an active shielding, i.e., in addition to the effective portions of the gradient coils 11 on the curved surfaces 12, gradient shielding coils 16 are provided on likewise curved surfaces 13, as is shown schematically in section in FIG. 4. The gradient shielding coils 16 compensate the magnetic field produced by the effective portions of gradient coils in the direction of the inner wall of the magnet.

In standard gradient coil arrangements with active shielding, the gradient shielding coils are generally arranged parallel to the gradient useful coils. In contrast, in the exemplary embodiment according to FIG. 4, the surfaces 13, on which the gradient shielding coils 16 are arranged, lie parallel to the inner wall of the magnet, and thereby comprise a greater curvature than the surfaces 12 of the gradient useful coils 11. The distance between the effective portions of the gradient coils and the gradient shielding coils is thereby maximized, at least in the center region. It is thus possible to use fewer conductors, with the same shielding effect, than in the case in which the surfaces 13 for the gradient shielding coils 16 are parallel to the gradient coils. Moreover, the reducing effect on the useful field, which is in principle always present given shielding coils, is less. The intermediate space between the effective portions of the gradient coils 11 and the gradient shielding coils 16 can, for example, be used to house cooling ducts 15, as shown in FIG. 4.

Figure 5:
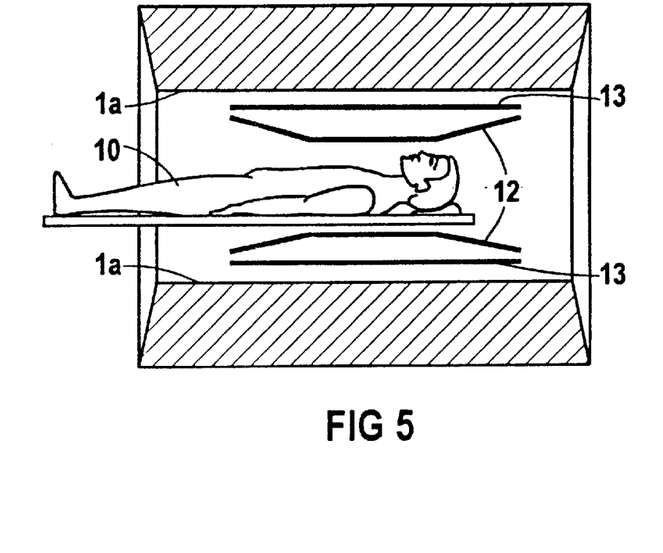
FIG. 5 shows a schematic longitudinal section of a first exemplary embodiment of a magnetic resonance apparatus having an inventive gradient coil apparatus.

As is shown in the schematic longitudinal section according to FIG. 5, the surfaces 12 may also have a curvature in longitudinal section, whereby the intermediate space expands outward. The following advantages are thereby achieved.

Patient accessibility is improved, and the patient feels less cramped, in an arrangement that expands outwardly. In the edge zones, the return conductors for the gradient coils are routed, which reduce the actually desired field. By means of the expansion, these return conductors are removed farther from the region of examination, so that their field-reducing effect becomes less. In addition, the gradient shielding coils are arranged parallel to the magnet inner wall, on surfaces 13.

Figure 6:
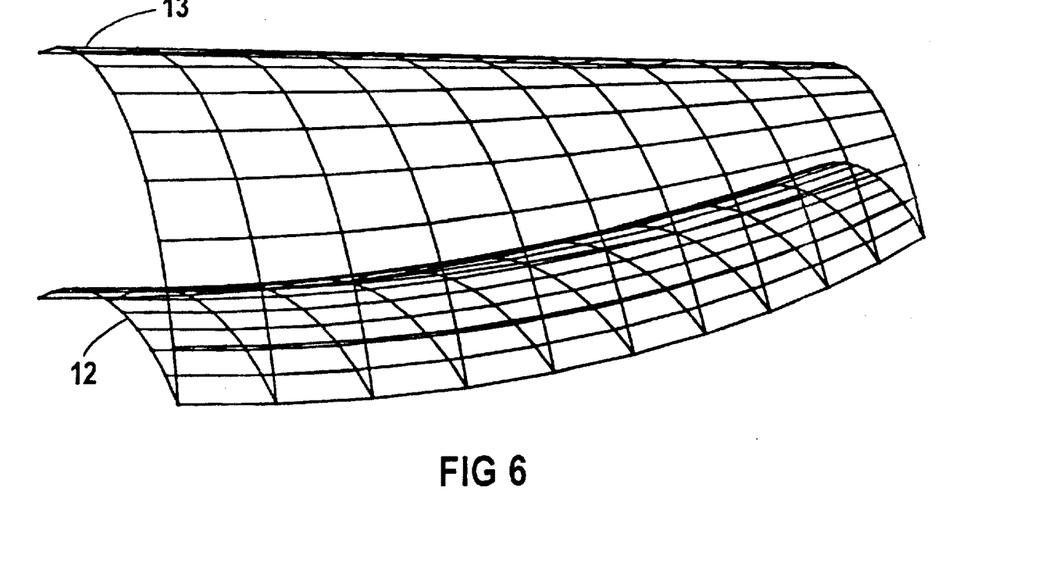
FIG. 6 shows a three-dimensional representation of the surfaces on which useful portions of the gradient coils and gradient shielding coils are located, in the inventive arrangement.

FIG. 6 shows a three-dimensional representation of a surface 12 for the gradient useful coils and a surface 13 for the gradient shielding coils.

Figure 7:
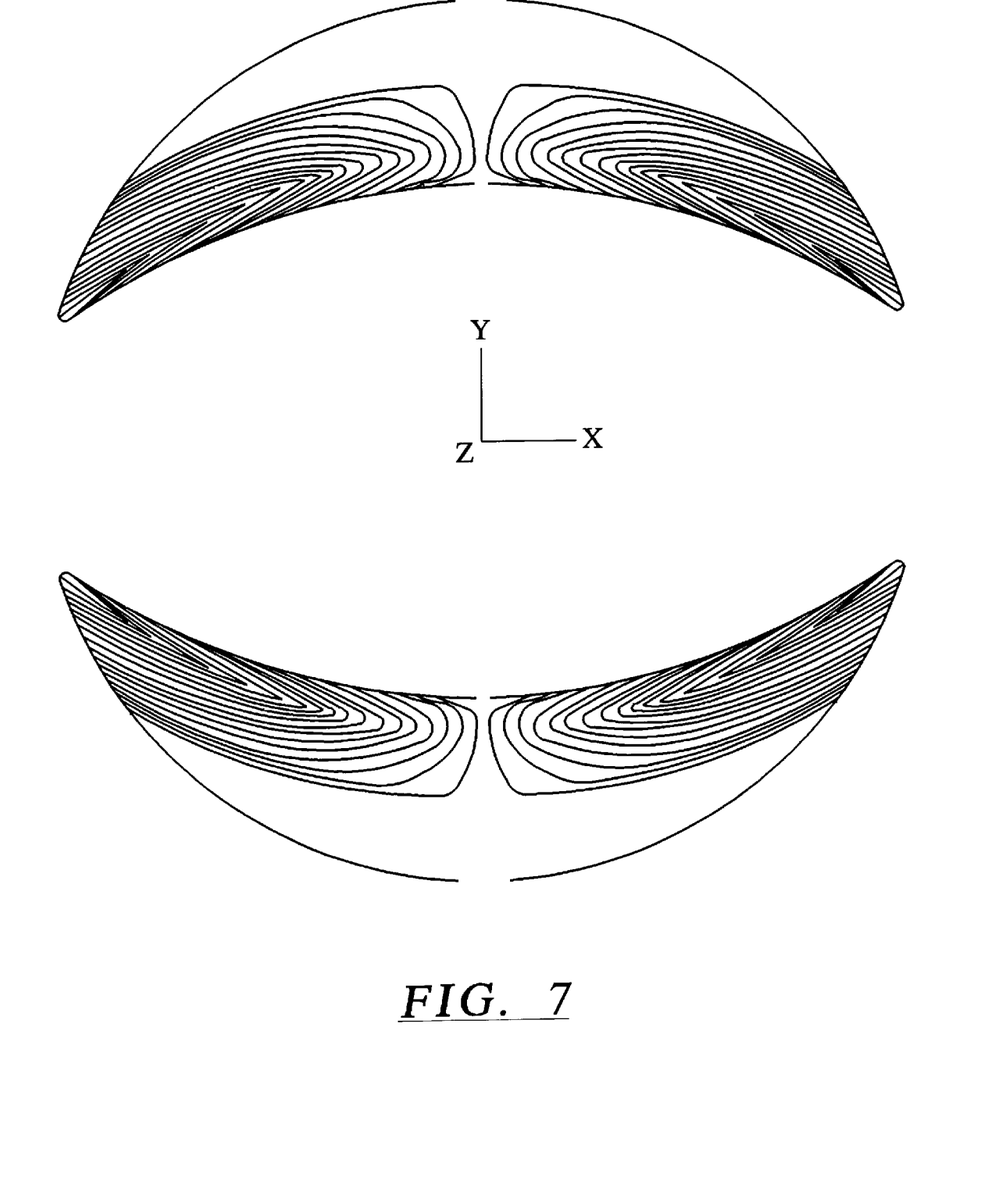
FIG. 7 shows a sectional view of a somewhat simplified conductor routing for the inventive gradient coil arrangement, in a direction perpendicular to the axis.
Figure 8:
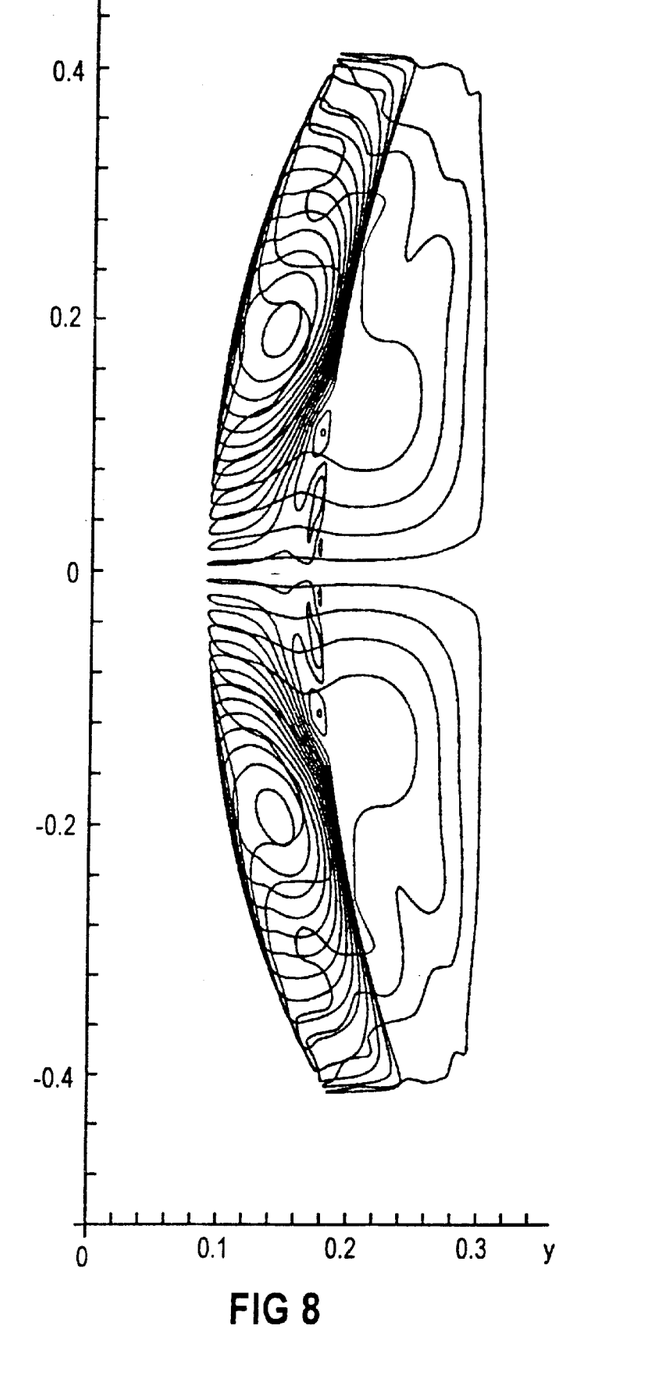
FIG. 8 shows a somewhat simplified conductor routing for one half of the inventive gradient coil arrangement, in longitudinal section.

The determination of the conductor routing in order to obtain the desired gradient field can ensue corresponding to the method disclosed in U.S. Pat. No. 5,309,107. FIG. 7 shows a conductor routing for a gradient coil in cross-projection, i.e. in x-y projection according to the convention in FIG. 2. FIG. 8 shows a conductor routing for a gradient coil in longitudinal projection, i.e. in y-z projection. The curvature of the coils in the respective plane can be seen clearly.

Figure 9:
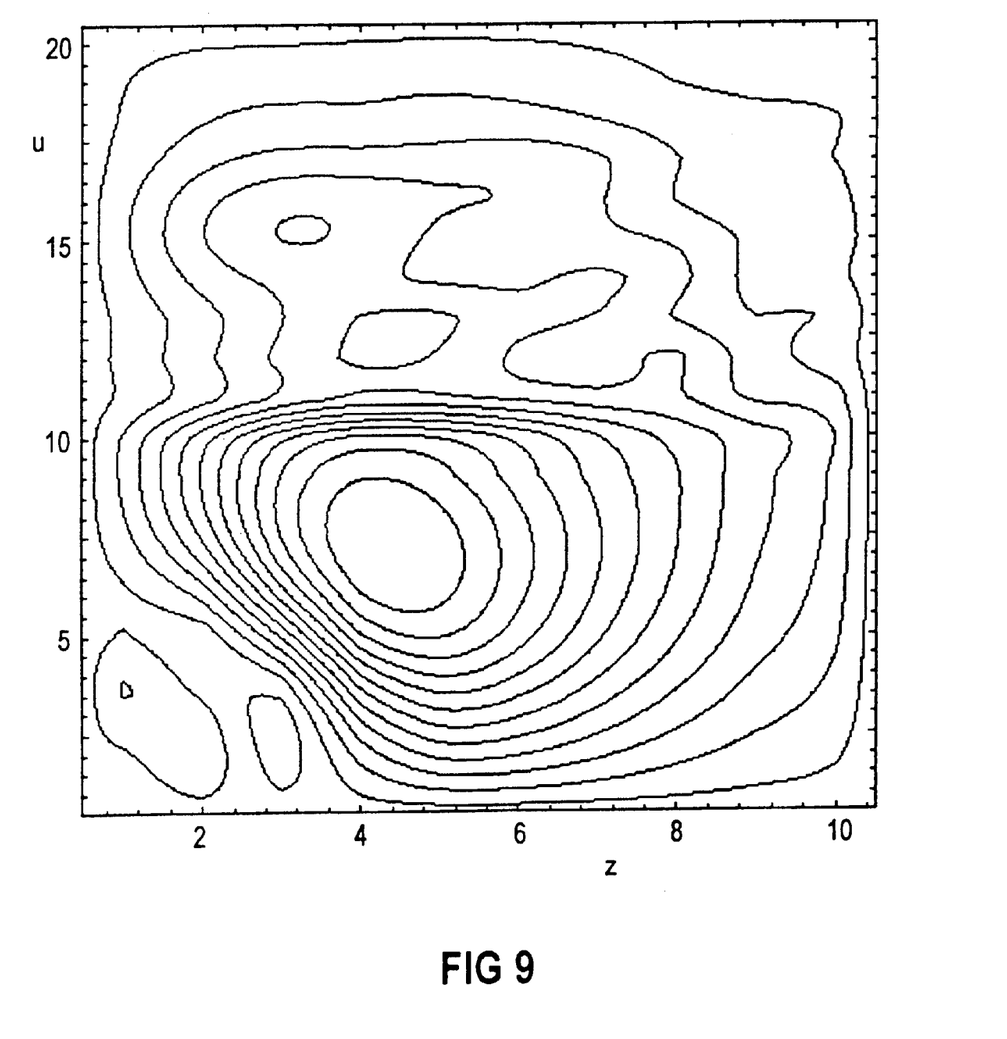
FIG. 9 shows a development of a surface of the inventive gradient coil for the x-direction, with the corresponding conductor routing.

FIG. 9 shows an embodiment of a gradient coil for producing an x-gradient. The gradient shielding coil is also developed for this purpose. Only an eighth of the overall coil is shown; all the other parts of the coil result due to symmetry. In each of FIGS. 7 to 9, the supply conductors have been omitted for clarity.

Figure 10:
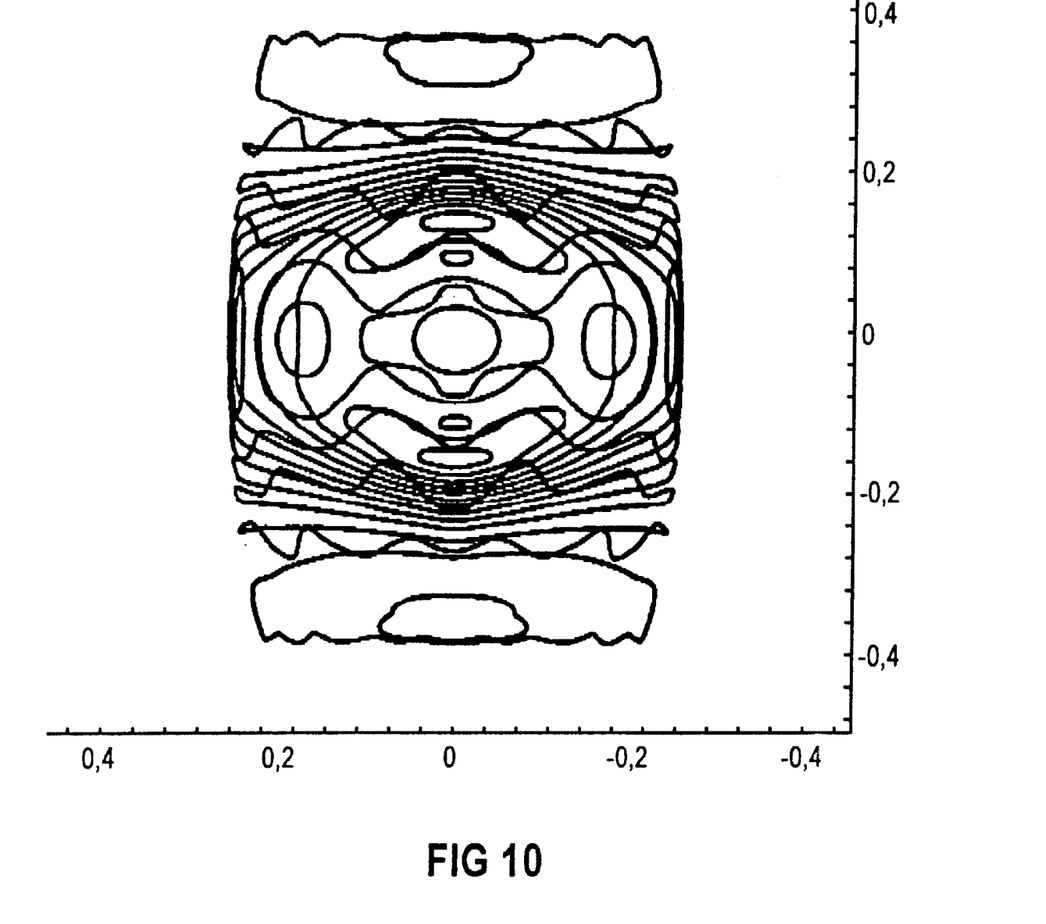
FIG. 10 shows a top view of the conductor routing of a z-gradient coil, in the inventive arrangement.

Finally, FIG. 10 shows a top view of the gradient coil for the z-direction.

Figure 11:
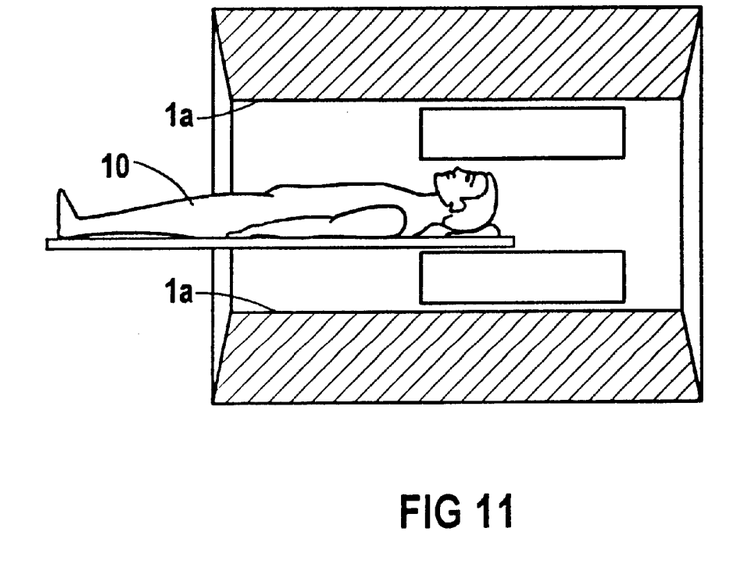
FIG. 11 shows a system with an examination region lying asymmetrically in an inventive gradient coil system.

Modern methods of calculating the conductor routing of gradient coils, such as for example the method described in the above-cited U.S. Pat. No. 5,309,107, enable great flexibility with respect to the desired field curve. Thus, it is possible to design e.g. gradient coils in such a way that the examination region, in which the desired linearity of the gradients is maintained, does not lie in the center of the gradient coil system, but rather is displaced toward the edge. The examination subject (e.g. the head of a patient according to FIG. 11) thus need not be inserted up to the center of the gradient coil system. Two things are thereby achieved. First, in special systems (e.g. for head examinations) the nuclear magnetic resonance tomography apparatus can be constructed still smaller, since the gradient coil system no longer has to pick up signals over the entire body, but rather only a part thereof. Second, a positioning of the head of the patient at the edge of the gradient coil system is more pleasant for the patient than in the center.

Figure 12:
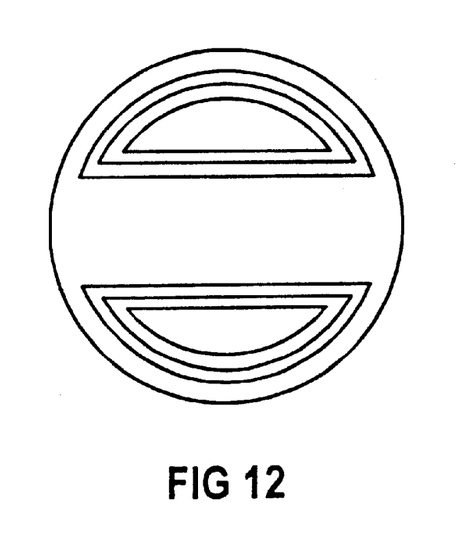
FIG. 12 shows an inventive interleaved gradient coil arrangement for the three spatial directions.

As stated above, in nuclear magnetic resonance tomography, locus resolution in three spatial directions (i.e., x, y, z in a Cartesian coordinate system) also requires gradients in three spatial directions. Thus, three gradient coils independent of one another must be provided. From the point of view of manufacturing technology, penetrations among the individual gradient coils are difficult to produce. It is possible to minimize such penetrations if (as shown in the schematic representation in FIG. 12) the three gradient coils are arranged on three shells that are interleaved with one another.

Although modifications and changes may be suggested by those skilled in the art, it is the intention of the inventors to embody within the patent warranted hereon all changes and modifications as reasonably and properly come within the scope of their contribution to the art.

We claim as our invention:

1. A gradient coil arrangement for a magnetic resonance tomography apparatus having a plurality of ring coils which produce a basic magnetic field and which enclose an examination chamber having a longitudinal axis, said ring coils having respective coil axes extending along said longitudinal axis, said gradient coil arrangement comprising:

first and second sets of coil conductors respectively disposed on opposite sides of said longitudinal axis, said first and second sets of coil conductors each having a plurality of segments which are effective for producing a gradient field, said segments in each of aid first and second sets of coil conductors being respectively disposed on two surfaces which are radially spaced from, and symmetrical to, said longitudinal axis, each segment having opposed sides disposed in a direction of, said longitudinal axis and a center disposed between said opposed sides, said opposed sides of said segments of said first set of coil conductors being spaced from said opposed sides of said second set of coil conductors to form opposed lateral spaces in said examination chamber extending in said direction of said longitudinal axis, and said segments and said surfaces having a curvature in a radial section, relative to said longitudinal axis, so that said surfaces and said segments of said first set of coil conductors have a spacing from said surfaces and said segments of said second set of coil conductors which is larger between the respective centers of said segments than between the respective edges of said segments.

2. A gradient coil arrangement as claimed in claim 1 wherein said examination chamber has an outer wall having an outer wall curvature, and wherein each of said surfaces has a curvature which is smaller than said outer wall curvature.

3. A gradient coil arrangement as claimed in claim 1 wherein said examination chamber has a center and opposed edges along said longitudinal axis, and wherein each of said surfaces and said segments has a curvature in an axial section, relative to said longitudinal axis, so that said segments and said surfaces have a smaller distance therebetween at said center of said examination chamber than at said edges of said examination chamber.

4. A gradient coil arrangement as claimed in claim 1 wherein said examination chamber has an outer wall, and further comprising gradient shielding coils disposed proximate to said outer wall of said examination chamber.

5. A gradient coil arrangement as claimed in claim 4 wherein said segments and said gradient shielding coils have a space therebetween, and said gradient coil arrangement further comprising cooling ducts disposed in said space.

6. A gradient coil arrangement as claimed in claim 4 comprising first, second and third sets of segments respectively oriented in three directions of an orthogonal coordinate system, and wherein said gradient shielding coils comprise three gradient shielding coil sets respectively disposed in said three directions of said orthogonal coordinate system, and wherein said three sets of segments and said three sets of gradient shielding coils are interleaved with each other.

7. A gradient coil arrangement as claimed in claim 1 wherein said conductors of said gradient coil arrangement are disposed so that said gradient coil arrangement is disposed asymmetrically relative to said examination chamber along said longitudinal axis.

\* \* \* \* \*